(12) United States Patent  
Miyahara

(10) Patent No.: US 8,764,637 B2
(45) Date of Patent: Jul. 1, 2014

(54) LIVING-BODY OBSERVATION SYSTEM AND DRIVING METHOD OF THE LIVING-BODY OBSERVATION SYSTEM

(75) Inventor: Hideharu Miyahara, Nagano (JP)

(73) Assignee: Olympus Corporation, Tokyo (JP)

( * ) Notice: Subject to any disclaimer, the term of this patent is extended or adjusted under 35 U.S.C. 154(b) by 361 days.

(21) Appl. No.: 12/754,076

(22) Filed: Apr. 5, 2010

(65) Prior Publication Data

US 2010/0261960 A1 Oct. 14, 2010

(30) Foreign Application Priority Data

Apr. 14, 2009 (JP) ................................ 2009-098167

(51) Int. Cl.
*A61B 1/04* (2006.01)
*A61B 1/00* (2006.01)

(52) U.S. Cl.
USPC ............ 600/118; 600/109; 600/103; 600/114

(58) Field of Classification Search
CPC .... A61B 1/041; A61B 1/00016; A61B 5/073; A61B 5/6861; A61B 5/076
USPC ......... 600/118, 409, 109, 101, 103, 107, 302, 600/114, 306, 104, 160, 420, 157, 476; 348/77, 65; 328/128
See application file for complete search history.

(56) References Cited

U.S. PATENT DOCUMENTS

| | | | | |
|---|---|---|---|---|
| 7,956,613 | B2 * | 6/2011 | Wald | 324/309 |
| 8,449,452 | B2 * | 5/2013 | Iddan et al. | 600/109 |
| 2004/0254455 | A1 * | 12/2004 | Iddan | 600/424 |
| 2006/0004255 | A1 * | 1/2006 | Iddan et al. | 600/160 |
| 2007/0191671 | A1 * | 8/2007 | Kawano et al. | 600/12 |
| 2007/0232870 | A1 * | 10/2007 | Mizuno | 600/302 |
| 2008/0125627 | A1 * | 5/2008 | Mizuno | 600/109 |
| 2009/0192351 | A1 * | 7/2009 | Nishino | 600/109 |

FOREIGN PATENT DOCUMENTS

JP 2005-193066 7/2005

* cited by examiner

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

A living-body observation system is provided with: an in-vivo observation apparatus including: an in-vivo information acquiring section; a power source section; a magnetic field detection section that detects a magnetic field from outside and outputs a detected result as an electric signal; and a power supply section that controls a supply state of driving power supplied to the in-vivo information acquiring section, and the operation of the in-vivo information acquiring section, based on the electric signal; and a magnetic field generating section that is disposed outside the in-vivo observation apparatus and generates the magnetic field, wherein the power supply section includes a control section that controls the operation of the in-vivo information acquiring section of the in-vivo observation apparatus.

16 Claims, 11 Drawing Sheets

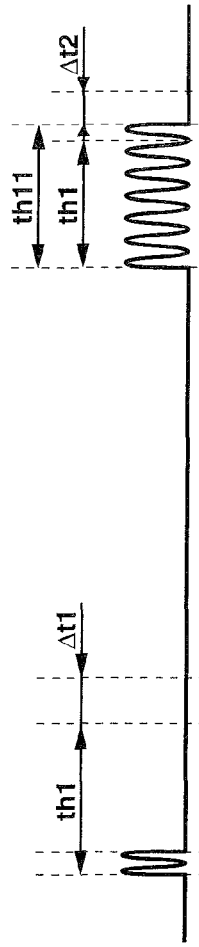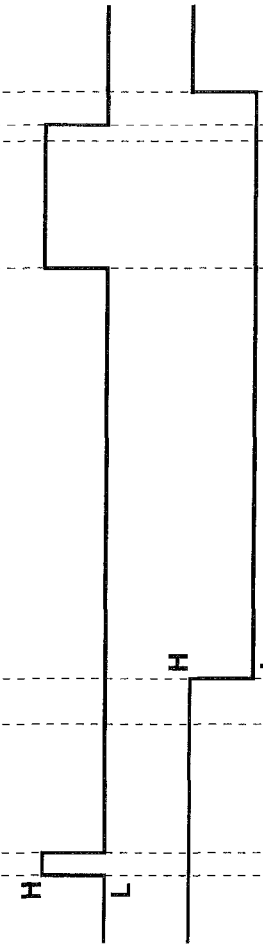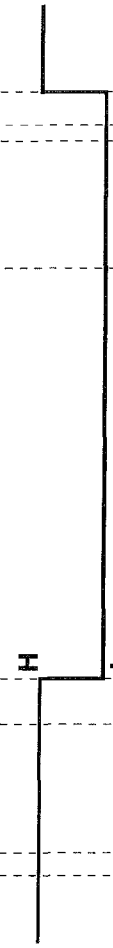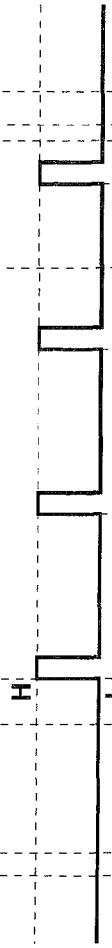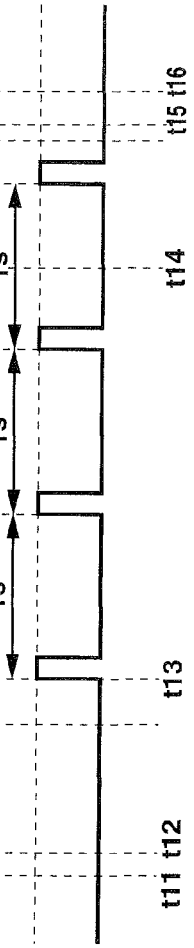

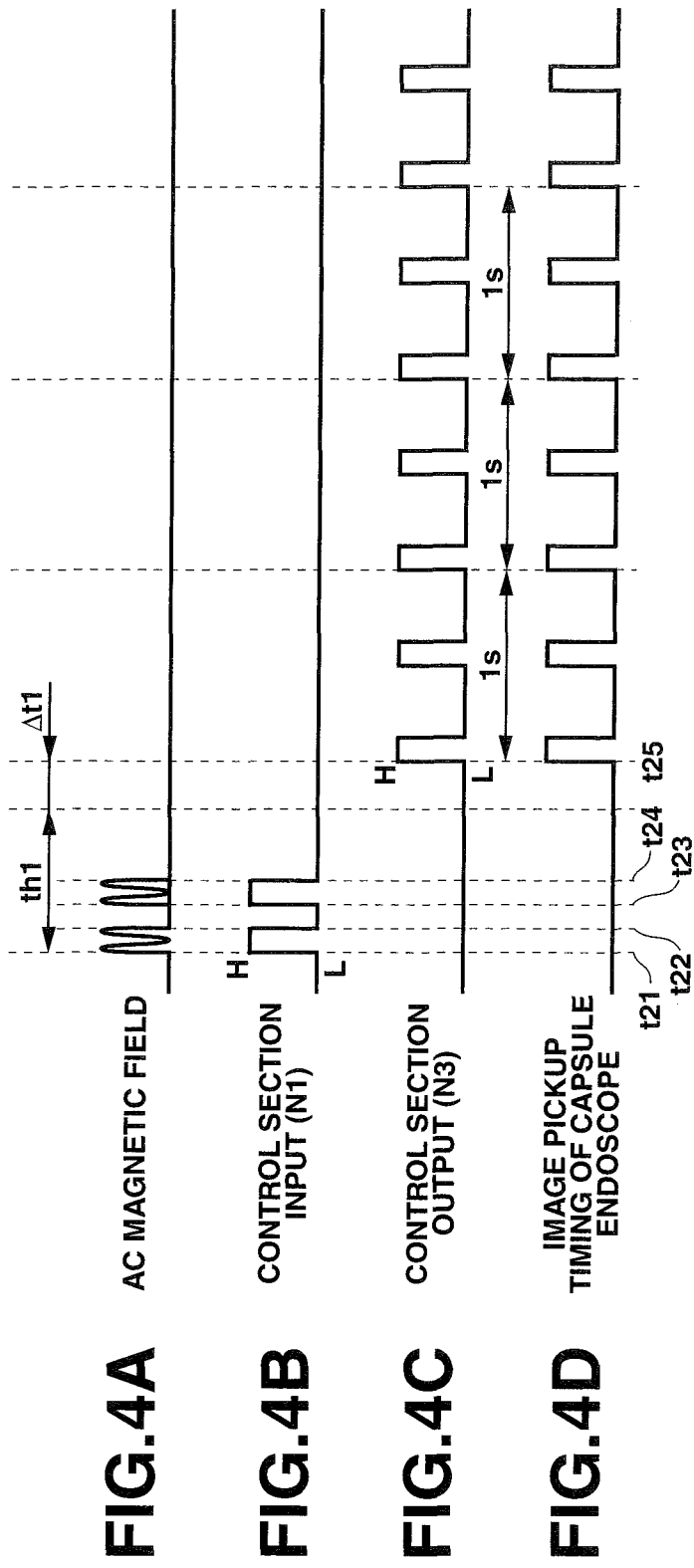

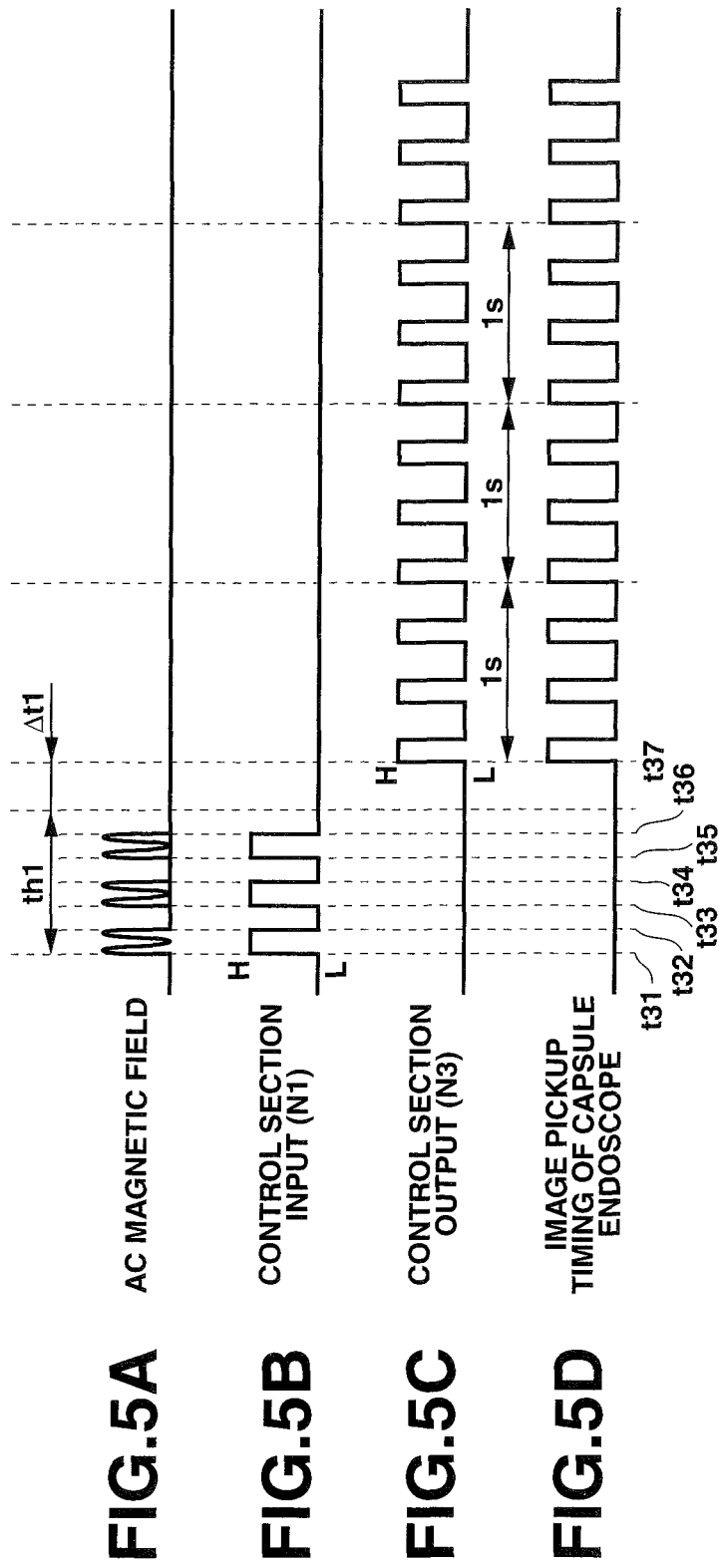

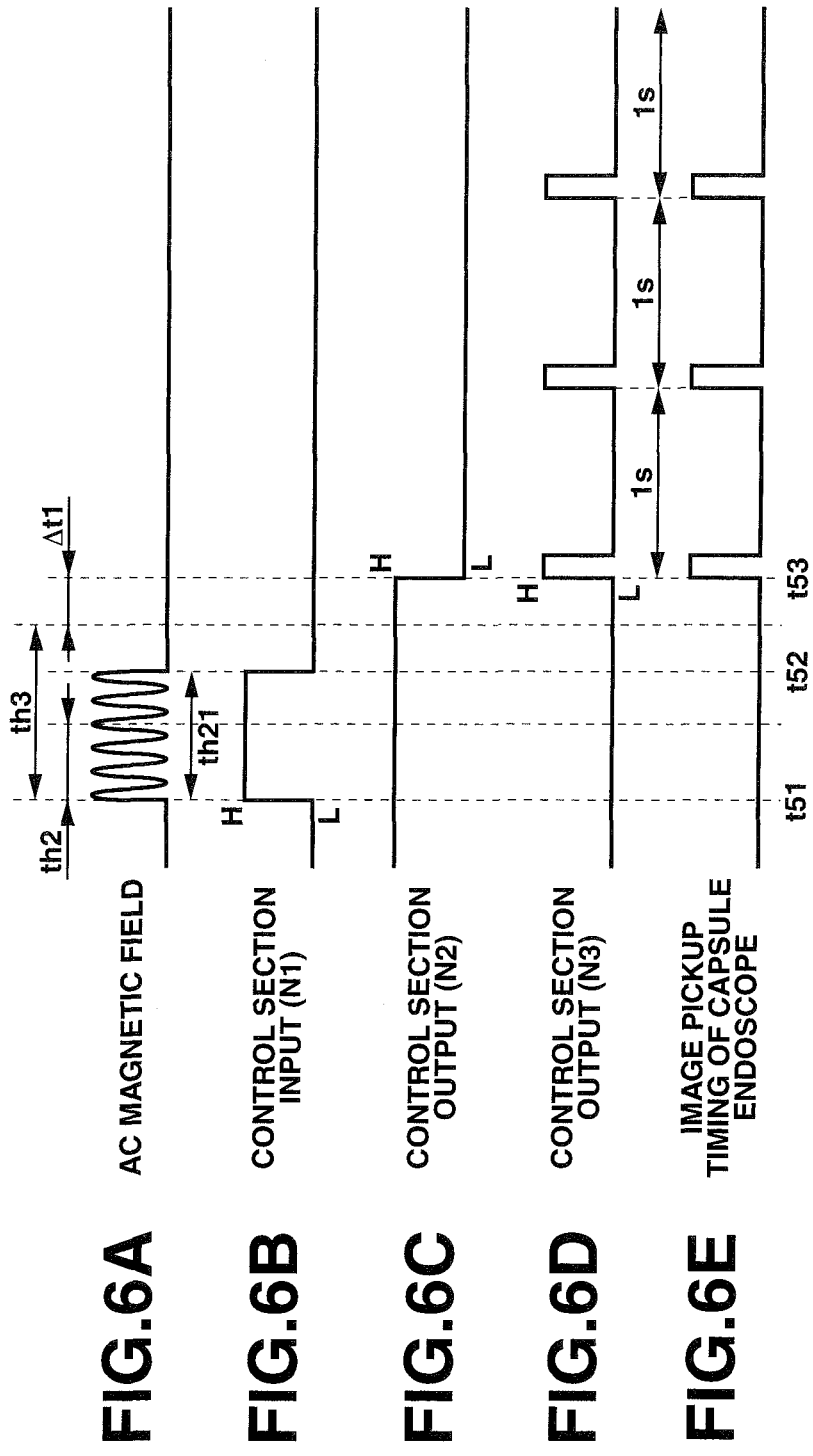

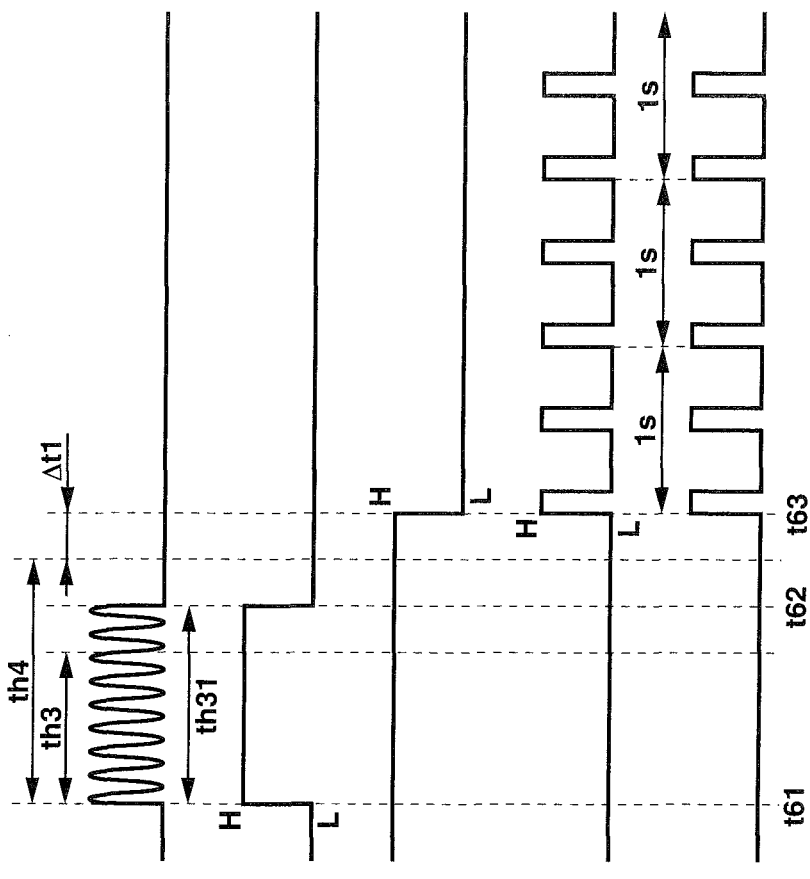

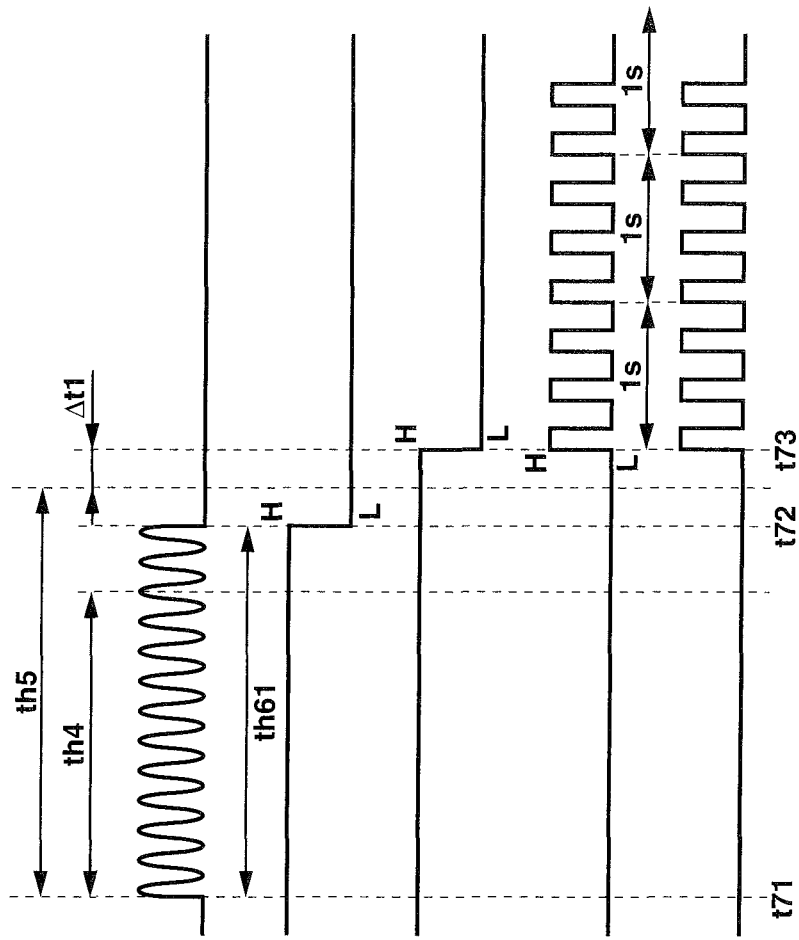

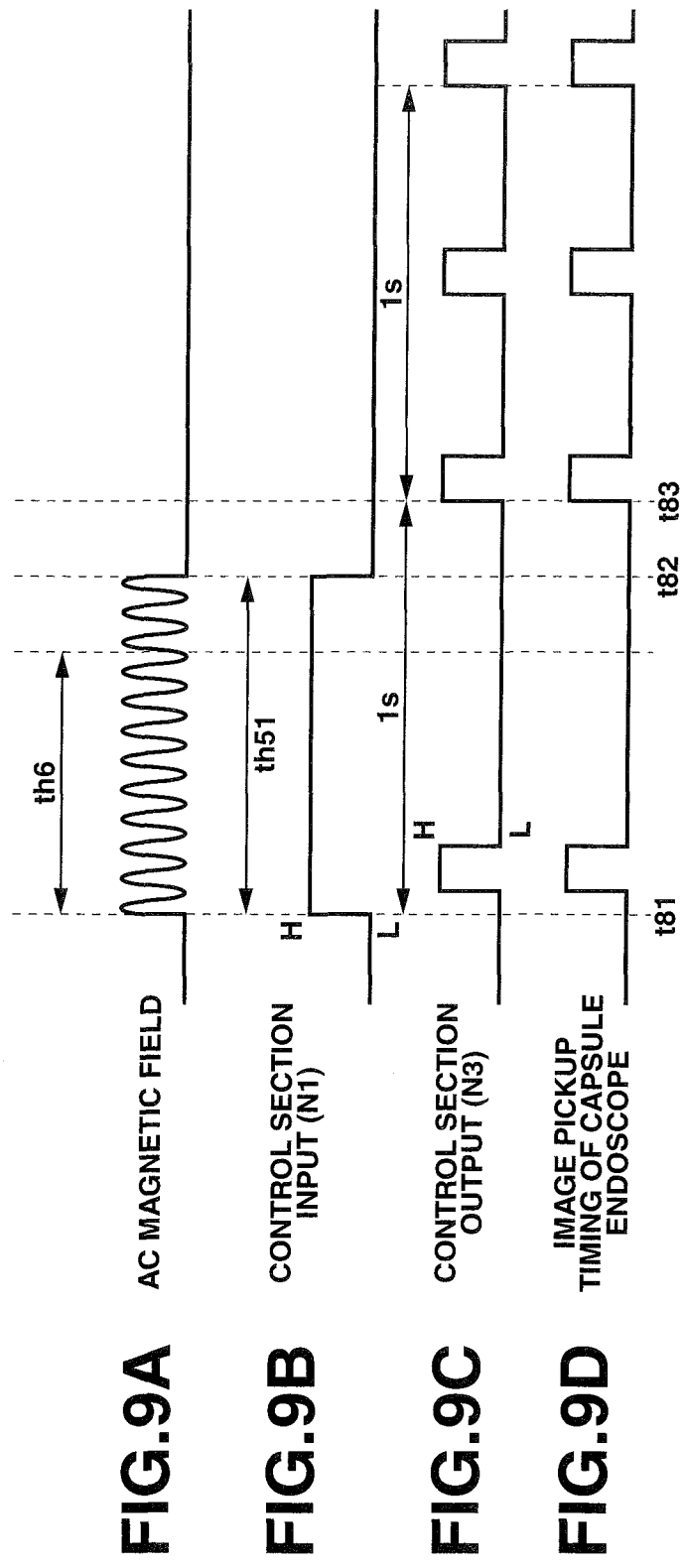

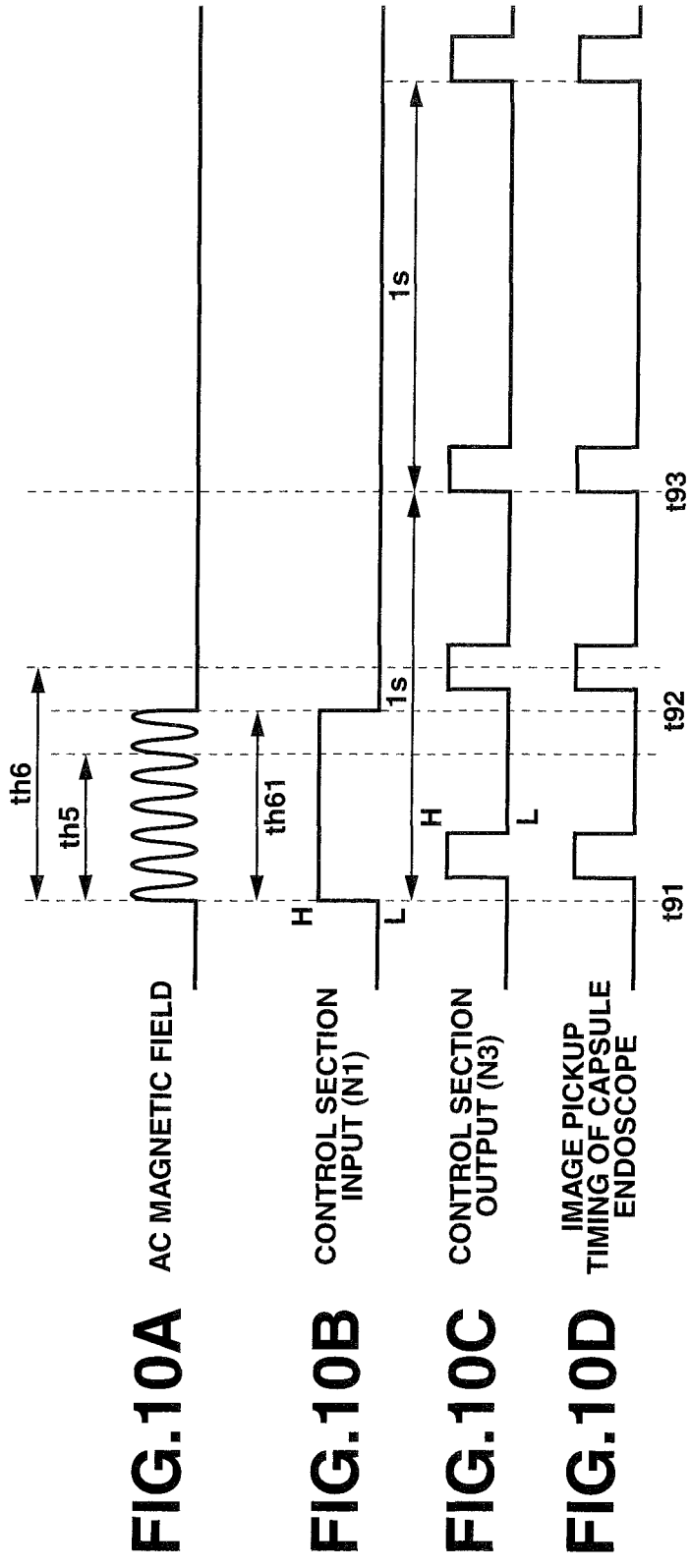

LIVING-BODY OBSERVATION SYSTEM AND DRIVING METHOD OF THE LIVING-BODY OBSERVATION SYSTEM

This application claims benefit of Japanese Application No. 2009-098167 filed in Japan on Apr. 14, 2009, the contents of which are incorporated by this reference.

BACKGROUND OF THE INVENTION

1. Field of the Invention

The present invention relates to a living-body observation system which can acquire information in a living body by means of an in-vivo observation apparatus, and a driving method of the living-body observation system.

2. Description of Related Art

Conventionally, endoscopes have been widely used in the medical field and others. In particular, endoscopes in the medical field are mainly used for the purpose of observing the inside of a living body. A capsule endoscope is proposed in recent years, as one type of the endoscopes described above, which is introduced into a body cavity by being swallowed by an examinee, and is capable of picking up images of inside the body cavity while being moved in the body cavity according to peristaltic movement, and wirelessly transmitting the picked-up images of inside the body cavity to outside as image pickup signals.

The capsule endoscopes which, as described above, moves in a body cavity while picking up images of inside the body cavity, include a type in which the number of images of inside a body cavity picked up in one second, that is, a frame rate is constant, and a type in which the frame rate is changed depending on the site to be observed.

Conventional capsule endoscopes in which the frame rate is changeable include, for example, a capsule endoscope proposed in Japanese Patent Application Laid-Open Publication No. 2005-193066. FIG. 12 is a longitudinal sectional view to schematically show the capsule endoscope disclosed in Japanese Patent Application Laid-Open Publication No. 2005-193066. Moreover, FIG. 13 is an explanatory diagram for use of the capsule endoscope of FIG. 12.

Japanese Patent Application Laid-Open Publication No. 2005-193066 discloses, as shown in FIG. 12, a technology relating to a capsule endoscope which is configured to accommodate an image pickup device 101, illumination means 102, an image signal processing circuit 103, a memory 104, an image information transmission circuit 105, a battery 106, a transmission antenna 107, and position detection means 108 in an endoscope capsule body 99 of a capsule endoscope 100 so that the position of the capsule endoscope 100 itself which moves in a body cavity is detected by the position detection means 108.

The capsule endoscope 100 according to Japanese Patent Application Laid-Open Publication No. 2005-193066 requires that an external body plate 109 made up of a magnetic plate, a conductive plate, or a magnetic coil, etc. is placed to the body of the examinee as shown in FIG. 13, to detect the position of the capsule endoscope 100 itself. It is noted that the use example shown in FIG. 13 shows a case in which the external body plate 109 is placed along the esophagus 121 of an examinee 120.

As described in Japanese Patent Application Laid-Open Publication No. 2005-193066, since the swallowed capsule endoscope 100 is configured such that the position detection means 108 installed thereinside reacts to the external body plate 109 thereby detecting the position of the capsule endoscope 100 itself, the external body plate 109 is disposed at, for example, a position corresponding to the esophagus 121 of the examinee as shown in FIG. 13. As a result of this, the position detection means 108 of the capsule endoscope 100 senses the external body plate 109 only when the capsule endoscope 100 is present below (near) the external body plate 109.

In this case, the capsule endoscope 100 judges that the capsule endoscope 100 itself is present in the esophagus 121 while the position detection means 108 inside the capsule main body 99 senses the external body plate 109. Thus, since the passing speed of the capsule endoscope 100 will be high when the capsule endoscope 100 is present in the esophagus 121, a photographing apparatus which includes an image pickup device 101 and illumination means 102, etc. operates so that more images are captured by the capsule endoscope 100.

On the other hand, when the position detection means 108 of the capsule endoscope 100 comes not to sense the external body plate 109, it is configured to judge that the capsule endoscope 100 has passed the esophagus 121 and the above described photographing apparatus operates so as to decrease the frame rate.

Therefore, as a result of being configured in this way, the capsule endoscope 100 described in Japanese Patent Application Laid-Open Publication No. 2005-193066 can control the frame rate depending on the site to be observed.

SUMMARY OF THE INVENTION

A living-body observation system of the present invention is provided with: an in-vivo observation apparatus including an in-vivo information acquiring section that acquires information in a living body, a power source section that supplies driving power of the in-vivo information acquiring section, a magnetic field detection section that detects a magnetic field from outside and outputs a detected result as an electric signal, and a power supply control section that controls a supply state of driving power supplied from the power source section to the in-vivo information acquiring section, and an operation of the in-vivo information acquiring section based on the electric signal; and a magnetic field generating section that is disposed outside the in-vivo observation apparatus and generates the magnetic field, wherein the power supply control section includes a control section that controls the operation of the in-vivo information acquiring section.

Moreover, a driving method of the in-vivo observation system of the present invention is a driving method for driving the above described living-body observation system, wherein a frame rate of the image pickup section in the in-vivo information acquiring section is set based on the number of applications or a period of application of the magnetic field that is applied to the in-vivo observation apparatus.

BRIEF DESCRIPTION OF THE DRAWINGS

FIGS. 3A to 3F are waveform diagrams to show operation waveforms of the respective principal parts of the capsule endoscope of the first embodiment;

FIGS. 4A to 4D are waveform diagrams to show operation waveforms of the respective principal parts when the number of generations of AC magnetic field is two;

FIGS. 5A to 5D are waveform diagrams to show operation waveforms of the respective principal parts in a case in which the number of generations of AC magnetic field is three;

FIGS. 6A to 6E are waveform diagrams to show operation waveforms of the respective principal parts relating to a second embodiment of the living-body observation system of the present invention;

FIGS. 7A to 7E are waveform diagrams to show operation waveforms of the respective principal parts in a case in which the application period of AC magnetic field is a period which is longer than a period th3 and shorter than a period th4;

FIGS. 8A to 8E are waveform diagrams to show operation waveforms of the respective principal parts in a case in which the application period of AC magnetic field is a period which is longer than a period th4 and shorter than a period th5;

FIGS. 9A to 9D are waveform diagrams to show operation waveforms of the respective principal parts in a case in which the frame rate of the image pickup section is increased during operation, relating to a third embodiment of the living-body observation system of the present invention;

FIGS. 10A to 10D are waveform diagrams to show operation waveforms of the respective principal parts in a case in which the frame rate of the image pickup section is decreased during operation;

DETAILED DESCRIPTION OF THE PREFERRED EMBODIMENTS

Hereafter, embodiments of the present invention will be described with reference to the drawings.

First Embodiment

A first embodiment of the living-body observation system of the present invention will be described by using FIGS. 1 to 5D.

Figure 1:
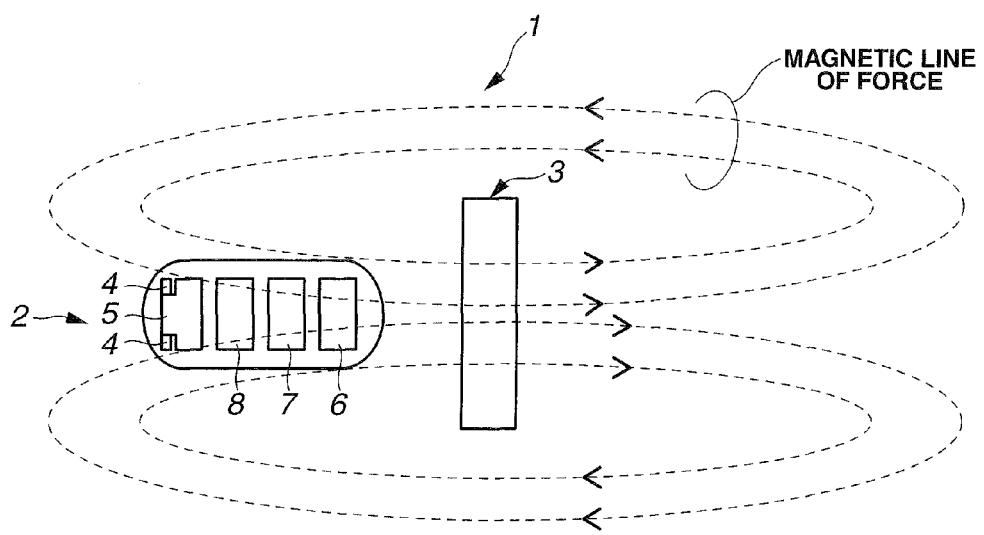
FIG. 1 is a configuration diagram to show the configuration of an entire living-body observation system relating to a first embodiment of the living-body observation system of the present invention.

FIG. 1 is a configuration diagram to show the configuration of an entire living-body observation system relating to the first embodiment.

As shown in FIG. 1, the living-body observation system 1 of the present embodiment is configured to include a capsule endoscope 2 that is configured to have a size and a shape, etc. that can be placed in a living body, and a magnetic field generating section 3 that is disposed outside the capsule endoscope 2 and generates an AC magnetic field.

The magnetic field generating section 3 is configured to be able to switch the generation state of magnetic field to either an ON state or an OFF state in response to, for example, the operation of a switch or the like which is not shown, by a user.

The capsule endoscope 2 as an in-vivo observation apparatus incorporates an in-vivo information acquiring section, which is configured to include at least an illumination section 4 that emits illumination light for illuminating an object to be photographed in a living body, and an image pickup section 5 that includes an objective optical system which is not shown to form an image of the object to be photographed illuminated by the illumination section 4, and outputs, as an image pickup signal, the image of the object to be photographed which is formed by the objective optical system.

Moreover, the capsule endoscope 2 incorporates a wireless transmission section 6 for transmitting a video signal acquired by the image pickup section 5 to outside the body, a power supply section 7 as a power supply control section that supplies driving power to the illumination section 4, the image pickup section 5, and the wireless transmission section 6 and controls the supply of the driving power, and a magnetic field detection section 8 that detects an AC magnetic field generated from outside.

It is noted that an outer casing of the capsule endoscope 2 is configured to be a dome-like lens shape having a transparent end part which is equipped with an image pickup device which is not shown. Moreover, the remaining cylindrical part and the opposite end part of the outer casing are made up of a light shielding material.

Next, specific configurations of the power supply section 7 and the magnetic field detection section 8 of the capsule endoscope 2 of FIG. 1 will be described by using FIG. 2.

Figure 2:
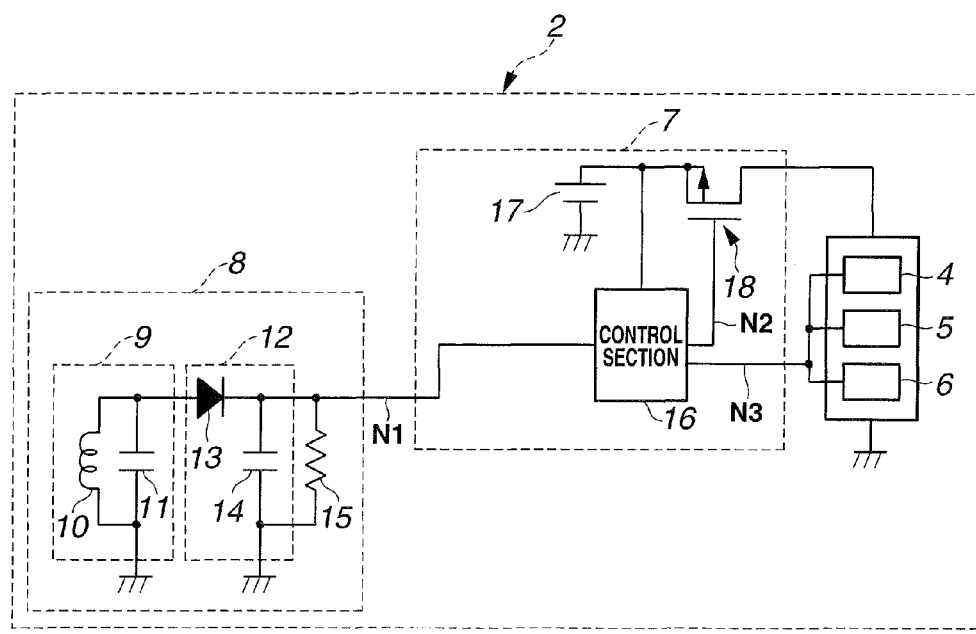
FIG. 2 is a block diagram to show an example of the internal configuration of the capsule endoscope of FIG. 1.

FIG. 2 is a block diagram to show an example of the internal configuration of the capsule endoscope of FIG. 1.

As shown in FIG. 2, the magnetic field detection section 8 is configured to include a receiving antenna 9 that outputs an electric signal in accordance with an AC magnetic field generated at the magnetic field generating section 3, a rectifying section 12 that rectifies and outputs the electric signal outputted from the receiving antenna 9, and a resistor 15.

The receiving antenna 9 is configured to include, for example, a magnetic field detection coil 10 that outputs an electric signal in accordance with an AC magnetic field generated at the magnetic field generating section 3, and a resonance capacitor 11 that is connected in parallel to the magnetic field detection coil 10 at an input end of the rectifying section 12.

The rectifying section 12 includes a diode 13, an input end of which is connected to the output end of the receiving antenna 9, and a smoothing capacitor 14 that smoothes the electric signal outputted from the diode 13.

The resistor 15 is connected in parallel to the smoothing capacitor 14 at the output end of the diode 13.

An output end which is via the connecting point between the resistor 15 and the smoothing capacitor 14, that is, an output end (node N1 which is also an input end of a control section 16) of the magnetic field detection section 8 is, as shown in FIG. 2, connected to the control section 16 of the power supply section 7 and outputs its output as a magnetic detection signal to the control section 16 of the power supply section 7.

It is noted that the magnetic field detection coil 10 may be, for example, a kind of coil such as a solenoid type coil or a planar coil, and may be of any shape provided that it can be placed in the capsule endoscope 2.

On the other hand, as shown in FIG. 2, the power supply section 7 is configured to include a power source section 17 made up of a cell and the like, a P-channel type FET 18, and a control section 16 to which an output signal (detection signal) from the magnetic field detection section 8 is supplied.

The node N1 as an input end of the control section 16 is connected to an output end of the magnetic field detection section 8. That is, an electric signal outputted from the magnetic field detection section 8 is inputted to the control section 16 via the node N1. A node N2 as an output end of the control section 16 is connected to a gate of the P-channel type FET 18.

A source of the P-channel type FET 18 is connected to the power source section 17. Further, a drain of the P-channel type FET 18 is connected to the illumination section 4, the image pickup section 5, and the wireless transmission section 6, respectively.

Moreover, the control section 16 varies the respective signal to be supplied to the input end (node N2) of the P-channel type FET 18, and an input end (node N3) of the illumination section 4, the image pickup section 5, and the wireless transmission section 6, based on the output signal (detection signal) from the magnetic field detection section 8, to control the operations of the illumination section 4, the image pickup section 5, and the wireless transmission section 6, which make up an in-vivo information acquiring section.

It is noted that the control section 16 is configured by using, for example, a micro computer, a DSP (Digital Signal Processor), a FPGA (Field Programmable Gate Array), and the like.

Moreover, the placement of the illumination section 4, the image pickup section 5, and the wireless transmission section 6 shown in FIG. 2 is schematically illustrated for the sake of simplicity of description, and in reality they are configured in a placement shown in FIG. 1.

Further, the power supply section 7 is not limited to the configuration using the P-channel type FET 18, but may be configured by using an electronic switch and the like having a function as a similar switching section.

In the living-body observation system 1 of the present embodiment, when the capsule endoscope 2 is interlinked with an AC magnetic field generated by the magnetic field generating section 3 as shown in FIG. 1, a voltage is generated at both ends of the magnetic field detection coil 10 of the capsule endoscope 2 so that the output of the magnetic field detection section 8 becomes a high level (thereafter, referred to as a "High" level). On the other hand, when the capsule endoscope 2 is not interlinked with an AC magnetic field, no voltage is generated at both ends of the magnetic field detection coil 10, and thereby the output of the magnetic field detection section 8 becomes a low level (hereafter, referred to as a "Low" level).

Therefore, the capsule endoscope 2 is configured such that a "High" level signal is inputted to the control section 16 only during a period in which an AC magnetic field is being generated.

That is, in the capsule endoscope 2 of the present embodiment, since the control section 16 can control the operation of the illumination section 4, the image pickup section 5, and the wireless transmission section 6 based on an output signal (detection signal) of a "High" level or a "Low" level from the above described magnetic detection section 8, it becomes possible to easily control the frame rate of the image pickup section 5.

Next, the operation of the living-body observation system 1 in the present embodiment, specifically the operations of the magnetic field generating section 3, the power supply section 7, and the magnetic field detection section 8 will be described by using FIGS. 1 and 2, and FIGS. 3A to 3F.

It is noted that FIGS. 3A to 3F are waveform diagrams to show the operation waveforms of respective principal parts of FIG. 1 and FIG. 2, in which FIG. 3A shows an AC magnetic field generation state from the magnetic field generating section 3, FIG. 3B shows an input signal (N1) of the control section 16, FIG. 3C shows an output signal (N2) of the control section 16, FIG. 3D shows the operation state of the capsule endoscope, FIG. 3E shows an output signal (N3) of the control section 16, which is inputted to a P-channel type FET, and FIG. 3F shows the image pickup timing of the capsule endoscope, respectively.

First, an activation operation and a stop operation of the capsule endoscope 2 will be described.

In the capsule endoscope 2 of FIG. 2, the output signal of the control section 16 (the signal supplied to the node N2 of the input end of the P-channel type FET 18) is set to be a "High" level in advance as shown in FIG. 3C. In this state, since the P-channel type FET 18 is in an OFF state, power from a power source section 17 will not be supplied to the capsule endoscope 2, and therefore the capsule endoscope 2 is stopped as shown in FIG. 3D.

Then, as shown in FIG. 3A, an AC magnetic field is generated by the magnetic field generating section 3 during a period from time t11 to time t12. Thus, the generated AC magnetic field is applied to the capsule endoscope 2, and the input signal (node N1) of the control section 16 becomes a "High" level only during a period in which the AC magnetic field is applied (see FIG. 3B).

When a "High" level signal (node N1) is inputted to the control section 16 in a state in which the output signal (node N2) of the control section 16 is in a state of "High" level, that is, in a state in which the capsule endoscope 2 is stopped, the control section 16 judges that the capsule endoscope 2 is activated, and sets the output signal (node N2) of the control section 16 to a "Low" level at time t13 (see FIG. 3C).

As a result of the output signal (node N2) of the control section 16 being set to a "Low" level, and thereby the P-channel type FET 18 turning to an ON state, power from the power source section 17 is supplied to the capsule endoscope 2, and the capsule endoscope 2 will get activated (see FIG. 3D).

Here, a period th1 from time t11 is, as described below, a period in which the number of times an AC magnetic field is applied to the capsule endoscope 2 is counted, and a period in which a frame rate of the image pickup section 5 of the capsule endoscope 2 is controlled.

Next, if an AC magnetic field is applied to the capsule endoscope 2 during a period th11 from time t14 to time t15, a "High" level signal will be inputted to the control section 16, as shown in FIG. 3A, for a period th11 beyond a predetermined period th1.

At this time, since the capsule endoscope 2 is in an activated state as shown in FIG. 3D, as a result of a "High" level signal (node N1) being inputted to the control section 16 for a predetermined period th11, the control section 16 judges that the capsule endoscope 2 is to be stopped.

Then, at time t16, the control section 16 sets the output signal (node N2) of the control section 16 to a "High" level and outputs the signal. As a result of the output signal (node N2) of the control section 16 being set to a "High" level and thereby the P-channel type FET 18 turning to an OFF state, the power supply from the power source section 17 to the capsule endoscope 2 will be stopped and thereby causing the capsule endoscope 2 to stop (see FIG. 3D).

It is noted that the period th11 in which an AC magnetic field is continuously generated is a period in which the stop of the capsule endoscope 2 is controlled, and is longer than the period th1. Further, in a second embodiment described below as well, when this period th11 is utilized, the period th11 is configured to be a period longer than the period th1 and not longer than the period th2.

Thus, since the start and stop of power supply is switched by the application state of AC magnetic field to the control section 16, and the operation state of the control section 16 when an AC magnetic field is applied; it becomes possible to control the switching of the state of the capsule endoscope 2 from a stopped state to an activated state, or an activated state to a stopped state.

It is noted that Δt1 shown in FIG. 3A is a time needed until the control section 16 counts the number of times an AC magnetic field is applied during a period th1 by use of counting means not shown in the control section 16 and, based on the counting result of the number of times of the applied AC magnetic field, determines the frame rate in the image pickup section 5 of the capsule endoscope 2.

Moreover, Δt2 shown in FIG. 3A is a processing time needed until the control section 16 stops the operation of the capsule endoscope 2 after the application of the AC magnetic field is stopped.

Next, a method for controlling the frame rate of the image pickup section 5 in the control section 16 will be described.

In the present embodiment, the control section 16 controls the operation of the image pickup section 5 so as to set the frame rate when an image is picked up in a living body by the image pickup section 5, based on an electric signal (a detection signal, node N1) from the magnetic field detection section 8. In this case, the frame rate is set by the control section 16 based on the number of times an AC magnetic field is applied to the capsule endoscope 2.

For example, as shown in FIG. 3A, if an AC magnetic field is generated in a period from time t11 to time t12, a "High" level signal (node N1) is inputted to the control section 16.

Accordingly, after a period th1 has passed, the frame rate of the image pickup section 5 of the capsule endoscope 2 is determined at the control section 16 from the number of generations of AC magnetic field during this period, that is, the number pulses inputted to the control section 16. It is noted that in the example shown in FIGS. 3A to 3F, the AC magnetic field is generated once during a period th1.

Therefore, in the capsule endoscope 2, the image pickup section 5 will operate at 1 fps (an fps is the abbreviation of "frame per second" meaning a unit to represent the number of exposures to be taken per second. A case of 1 fps means that one image is taken in one second).

When the frame rate of the image pickup section 5 of the capsule endoscope 2 is determined by the control section 16, the output signal (node N2) of the control section 16 becomes a "Low" level at time t13, and at the same time, the control section 16 generates pulses at a rate of one time per second as shown in the output signal (node N3) of the control section 16 in FIG. 3E, and outputs the pulses to the image pickup section 5. Thus, the image pickup section 5 of the capsule endoscope 2 operates at 1 fps.

During this pulse generation period of the output signal (node N3) of the control section 16, the illumination section 4, the image pickup section 5, and the wireless transmission section 6 of the capsule endoscope 2 will be in an ON state: during this period, the observation of the inside of a body cavity is performed and one image is taken in one second by the image pickup section 5.

It is noted that during a period in which no pulse is generated, the capsule endoscope 2 is being activated; however, the illumination section 4, the image pickup section 5, and the wireless transmission section 6 are in a stand-by state.

Now, operations when the numbers of generations of AC magnetic field is two and three in the period th1 will be described by using FIGS. 4A to 4D, and FIGS. 5A to 5D.

It is noted that FIGS. 4A to 4D are waveform diagrams to show the operation waveforms of respective principal parts when the number of generations of AC magnetic field is two, in which FIG. 4A shows an AC magnetic field generation state (AC magnetic field is generated twice) from the magnetic field generating section 3, FIG. 4B shows the input signal (node N1) of the control section 16, FIG. 4C shows the output signal (node N3) of the control section 16 to be inputted to the P-channel type FET, and FIG. 4D shows image pickup timings of the capsule endoscope, respectively.

Moreover, FIGS. 5A to 5D are waveform diagrams to show the operation waveforms of respective principal parts when the number of generations of AC magnetic field is three, in which FIG. 5A shows an AC magnetic field generation state (AC magnetic field is generated 3 times) from the magnetic field generating section 3, FIG. 5B shows the input signal (N1) of the control section 16, FIG. 5C shows the output signal (N3) of the control section 16 to be inputted to the P-channel type FET, and FIG. 5D shows image pickup timings of the capsule endoscope, respectively.

For a case in which the number of generations of AC magnetic field is two during a period th1 as well, the control section 16 operates in a similar fashion to the operation example shown in FIGS. 3A to 3F.

That is, as shown in FIG. 4A, when an AC magnetic field is generated twice from time t21 to time t22, and from time t23 to time t24 within the period th1, the input signal (node N1) of the control section 16 also becomes a "High" level twice within the period th1 (see FIG. 4B).

Therefore, the control section 16 sets the frame rate of the image pickup section 5 to 2 fps, and generates pulses at a rate of two pulses per second to output them to the image pickup section 5 as shown in the output signal (node N3) of the control section 16 of FIG. 4C. As a result of this, the image pickup section 5 of the capsule endoscope 2 operates at 2 pfs at and after time t25, in which the observation inside the body cavity is performed and two images are taken in one second by the image pickup section 5.

For a case in which the number of generations of AC magnetic field is three during a period th1 as well, the control section 16 operates in a similar fashion to the operation example shown in FIGS. 3A to 3F.

That is, as shown in FIG. 5A, when an AC magnetic field is generated three times from time t31 to time t32, from time t33 to time t34, and from time t35 to time t36 within the period th1, the input signal (node N1) of the control section 16 also becomes a "High" level three times within the period th1 (see FIG. 5B).

Therefore, the control section 16 sets the frame rate of the image pickup section 5 to 3 fps, and generates pulses at a rate of three pulses per second to output them to the image pickup section 5 as shown in the output signal (node N3) of the control section 16 of FIG. 5C. As a result of this, the image pickup section 5 of the capsule endoscope 2 operates at 3 pfs at and after time t37, in which the observation inside the body cavity is performed and three images are taken in one second by the image pickup section 5.

Thus, in the living-body observation system 1 of the present embodiment, the frame rate in picking up images by the image pickup section 5 of the capsule endoscope 2 is set in accordance with the number of times an AC magnetic field is applied to the capsule endoscope 2, by counting the number of times an AC magnetic field is applied to the capsule endoscope 2 within a predetermined period th1 in which the number of applications of AC magnetic field is counted.

It is noted that although, in the present embodiment, description has been made on a case in which the timing at which the output signal (node N3) of the control section 16 becomes a "High" level coincides with the timing at which the illumination section 4, the image pickup section 5, and the wireless transmission section 6 operate; the timing at which the output signal (node N3) of the control section 16 becomes a "High" level does not necessarily need to coincide with the timing at which the illumination section 4, the image pickup section 5, and the wireless transmission section 6 operate.

For example, the output signal (node N3) of the control section 16 may serve as a trigger signal for operating the illumination section 4, the image pickup section 5, and the wireless transmission section 6. That is, the timing may be configured such that the illumination section 4, the image pickup section 5, and the wireless transmission section 6 operate after a fixed time has passed after the output signal (node N3) of the control section 16 becomes a "High" level.

Figure 12:
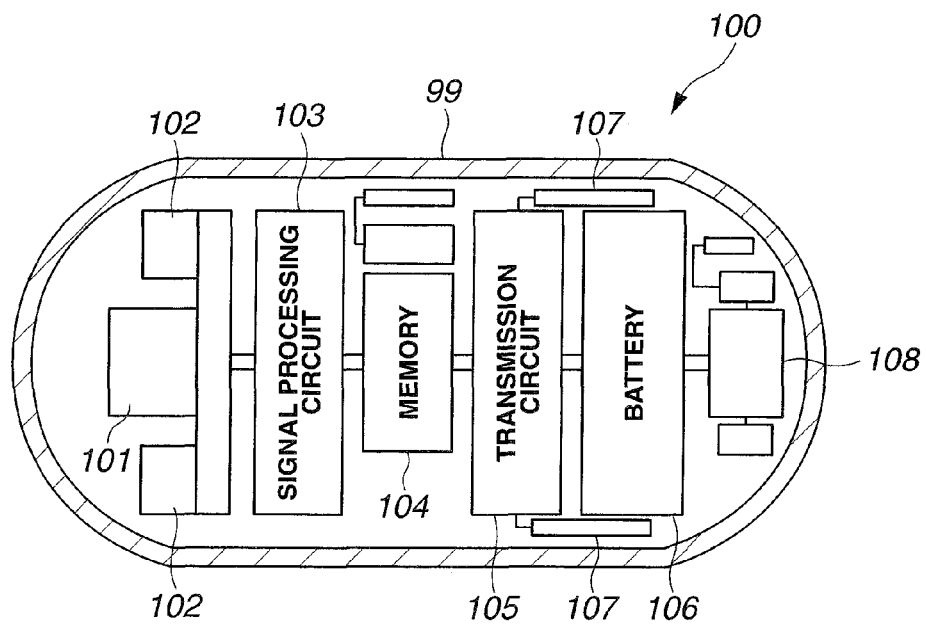
FIG. 12 a longitudinal sectional view to schematically show the capsule endoscope that is disclosed in Japanese Patent Application Laid-Open Publication No. 2005-193066.
Figure 13:
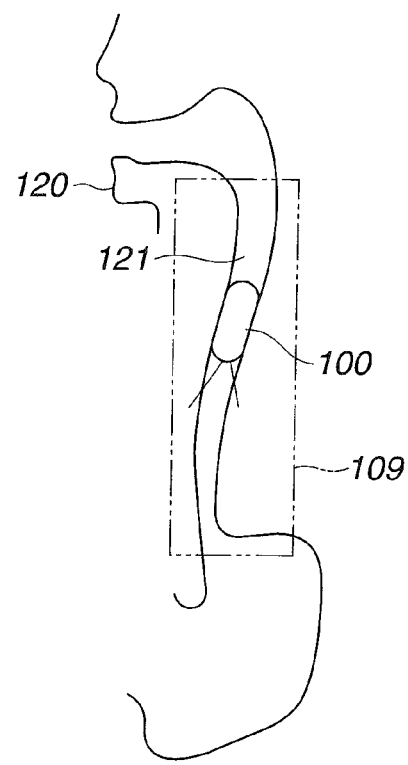
FIG. 13 is an explanatory diagram for use of the capsule endoscope of FIG. 12.

As with the present embodiment describe above, setting the frame rate of the image pickup section 5 in accordance with the number of times an AC magnetic field is applied to the capsule endoscope 2 will obviate the need of providing position detection means 108 (see FIG. 12) inside the capsule endoscope 2, and also will obviate the need of mounting a external body plate 109 (see FIG. 13) on the body of an examinee, making it possible to set the frame rate in the image pickup section of the capsule endoscope 2 with a simpler configuration.

Moreover, since the position detection means 108 and the external body plate 109 are not necessary, it is possible to reduce the components of the living-body observation system 1 thereby reducing the cost of the living-body observation system 1.

Therefore, according to the first embodiment, since the frame rate can be set in accordance with the number of times an AC magnetic field is applied to the capsule endoscope 2, it becomes possible to control the frame rate of the capsule endoscope 2 by means of a simpler system even if an external body plate is placed on the outside of the body of an examinee.

Further, reducing the components of the living-body observation system 1 will make it possible to achieve effects such as preventing the scaling up and reducing the cost of the living-body observation system 1.

Second Embodiment

FIGS. 6A to 6E are waveform diagrams to show the operation waveforms of respective principal parts of a second embodiment of the living-body observation system of the present invention, in which FIG. 6A shows an AC magnetic field generation state from the magnetic field generating section 3, FIG. 6B shows an input signal (N1) of the control section 16, FIG. 6C shows an output signal (N2) of the control section 16, FIG. 6D shows the output signal (N3) of the control section 16 to be inputted to a P-channel type FET, and FIG. 6E shows the image pickup timing of the capsule endoscope, respectively.

The living-body observation system 1 of the second embodiment is configured in substantially the same manner with the first embodiment. Moreover, in the present embodiment, the control section 16 controls the operation of the image pickup section 5 so as to set the frame rate when picking up images of inside the living body with the image pickup section 5, based on the application period of the AC magnetic field to be applied to the capsule endoscope 2.

Next, the operation of the living-body observation system 1 in the second embodiment, specifically, the operations of the magnetic field generating section 3, the power supply section 7, and the magnetic field detection section 8 will be described with reference to FIGS. 6A to 6E.

The observation system 1 of the second embodiment monitors the length of time in which an AC magnetic field is applied to the capsule endoscope 2 to compare the period of the application of the AC magnetic field with a predetermined period, and based on the comparison result, sets the frame rate in the image pickup section of the capsule endoscope 2

As shown in FIG. 6A, when an AC magnetic field is generated, and the AC magnetic field is applied to the capsule endoscope 2 for a period th21 from time t51 to time t52, the input signal (node N1) of the control section 16 also becomes a "High" level during the period th21 (see FIG. 6B). This period th21 is longer than a period th2 and not longer than a period th3.

It is noted that the period th2 and the period th3 are periods in which the application time of the AC magnetic field applied to the capsule endoscope 2 is measured, and the frame rate is controlled, and are predetermined so as to satisfy the relationship: the period th2<the period th3. Further, the period th2 is set to be longer than the period th1 in the first embodiment.

Here, in the second embodiment, since the application period of AC magnetic field is longer than the period th2 and not longer than the period th3, the control section 16 sets the frame rate of the image pickup section 5 of the capsule endoscope 2 to 1 fps.

When the frame rate of the capsule endoscope 2 is set by the control section 16, the output signal (node N2) of the control section 16 becomes a "Low" level at time t53, and at the same time, the control section 16 generates pulses at a rate of once per second to output them to image pickup section 5, as shown in the output signal (node N3) of the control section 16 of FIG. 6D. As a result of this, the image pickup section 5 of the capsule endoscope 2 operates at 1 fps.

During this pulse generation period of the output signal (node N3) of the control section 16, the illumination section 4, the image pickup section 5, and the wireless transmission section 6 of the capsule endoscope 2 turn into ON state, and during this period, the observation of the inside of a body cavity is performed and one image is taken in one second by the image pickup section 5.

It is noted that $\Delta t1$ shown in FIG. 6A is the time which is needed for the control section 16 to determine the frame rate based on the length of time in which an AC magnetic field is applied, as with the first embodiment.

Here, the operations in the cases in which the application period of AC magnetic field is longer than a period th3 and not longer than a period th4, and is longer than the period th4 and not longer than a period th5 will be described by using FIGS. 7A to 7E and FIGS. 8A to 8E.

It is noted that FIGS. 7A to 7E are waveform diagrams to show the operation waveforms of respective principal parts in a case in which the application period of AC magnetic field is longer than the period th3 and not longer than the period th4, in which FIG. 7A shows an AC magnetic field generation state from the magnetic field generating section 3, FIG. 7B shows an input signal (N1) of the control section 16, FIG. 7C shows an output signal (N2) of the control section 16, FIG. 7D shows the output signal (N3) of the control section 16 to be inputted to a P-channel type FET, and FIG. 7E shows the image pickup timing of the capsule endoscope, respectively.

Moreover, FIGS. 8A to 8E are waveform diagrams to show the operation waveforms of respective principal parts in a case in which the application period of AC magnetic field is longer than the period th4 and not longer than the period th5, in which FIG. 8A shows an AC magnetic field generation state from the magnetic field generating section 3, FIG. 8B shows an input signal (N1) of the control section 16, FIG. 8C shows an output signal (N2) of the control section 16, FIG. 8D shows the output signal (N3) of the control section 16 to be inputted to a P-channel type FET, and FIG. 8E shows the image pickup timing of the capsule endoscope, respectively.

In a case in which the application period th31 of AC magnetic field is longer than the period th3 and not longer than the period th4 as well, the control section 16 operates in the same manner as with the operation example shown in FIGS. 6A to 6E.

That is, as shown in FIG. 7A, when an AC magnetic field is generated for a period th31 from time t61 to time t62, which is longer than the period th3 and not longer than the period th4, and the AC magnetic field is applied to the capsule endoscope 2, the control section 16 sets the frame rate of the image pickup section 5 of the capsule endoscope 2 to 2 fps.

It is noted that here, the period th3 and the period th4 are periods in which the application time of the AC magnetic field applied to the capsule endoscope 2 is measured, and the frame rate is controlled, and are periods that satisfy the relationship: the period th3<the period th4.

When the frame rate of the capsule endoscope 2 is set by the control section 16, the output signal (node N2) of the control section 16 becomes a "Low" level at time t63 and at the same time, the control section 16 generates pulses at a rate of twice per second to output them to the image pickup section 5, as shown in the output signal (node N3) of the control section 16 of FIG. 7D. As a result of this, the image pickup section 5 of the capsule endoscope 2 operates at 2 fps.

During this pulse generation period of the output signal (node N3) of the control section 16, the illumination section 4, the image pickup section 5, and the wireless transmission section 6 of the capsule endoscope 2 turn into ON state, and during this period, the observation of the inside of a body cavity is performed and two images are taken in one second by the image pickup section 5.

It is noted that as with the first embodiment, Δt1 is the time which is needed for the control section 16 to determine the frame rate based on the length of time in which an AC magnetic field is applied.

Moreover, for a case in which the application period of AC magnetic field is longer than the period th4 and not longer than the period th5 as well, the control section 16 operates in the same manner as with the operation example shown in FIGS. 6A to 6E.

That is, as shown in FIG. 8A, when an AC magnetic field is generated for a period th61 from time t71 to time t72, which is longer than the period th4 and not longer than the period th5, and the AC magnetic field is applied to the capsule endoscope 2, the control section 16 sets the frame rate of the image pickup section 5 of the capsule endoscope 2 to 3 fps.

It is noted that here, the period th4 and the period th5 are periods in which the application time of the AC magnetic field applied to the capsule endoscope 2 is measured, and the frame rate is controlled, and are periods which satisfy the relationship: the period th4<the period th5.

When the frame rate of the capsule endoscope 2 is set by the control section 16, the output signal (node N2) of the control section 16 becomes a "Low" level at time t73 and at the same time, the control section 16 generates pulses at a rate of three times per second to output them to the image pickup section 5, as shown in the output signal (node N3) of the control section 16 of FIG. 8D. As a result of this, the image pickup section 5 of the capsule endoscope 2 operates at 3 fps.

During this pulse generation period of the output signal (node N3) of the control section 16, the illumination section 4, the image pickup section 5, and the wireless transmission section 6 of the capsule endoscope 2 turn into ON state, and during this period, the observation of the inside of a body cavity is performed and three images per second are photographed by the image pickup section 5.

It is noted that as with the first embodiment, Δt1 is the time which is needed for the control section 16 to determine the frame rate based on the length of time in which an AC magnetic field is applied.

Moreover, although in the second embodiment, description has been made on the case in which the frame rate increases as the application period of the AC magnetic field applied to the capsule endoscope 2 becomes longer, it is not necessary that the frame rate is increased as the application period of the AC magnetic field applied to the capsule endoscope 2 becomes longer, and on the contrary it may be set such that the frame rate is decreased as the application period of the AC magnetic field applied to the capsule endoscope 2 becomes longer.

Further, as with the first embodiment, in the second embodiment as well, it is assumed that when an AC magnetic field is applied to the capsule endoscope 2 for a period longer than the period th1 and not longer than the period th2 while the capsule endoscope 2 is operating, the capsule endoscope 2 is to be stopped.

That is, the living-body observation system 1 of the second embodiment is able to set the frame rate of the image pickup section 5 of the capsule endoscope 2, by changing not only the number of times an AC magnetic field is applied within a fixed period, but also the period in which the AC magnetic field is applied.

As a result of this, since as with the first embodiment, the living-body observation system 1 of the second embodiment need neither position detection means 108 (see FIG. 13) to be provided inside the capsule endoscope 2, nor an external body plate 109 (see FIG. 12) to be mounted on the body of an examinee, it is possible to set the frame rate in the image pickup section of the capsule endoscope 2 by means of a simpler configuration.

Moreover, since the position detection means 108 and the external body plate 109 are not necessary, it is possible to reduce the components of the living-body observation system 1 thereby reducing the cost of the living-body observation system 1.

Therefore, according to the second embodiment, since the frame rate can be set in accordance with the length of the application period of the AC magnetic field applied to the capsule endoscope 2, it becomes possible to control the frame rate of the capsule endoscope 2 by means of a simpler system even if an external body plate is not mounted on the outside of the body of an examinee.

Further, reducing the components of the living-body observation system 1 will achieve effects such as preventing the scaling up and reducing the cost of the living-body observation system 1.

Third Embodiment

Figure 11:
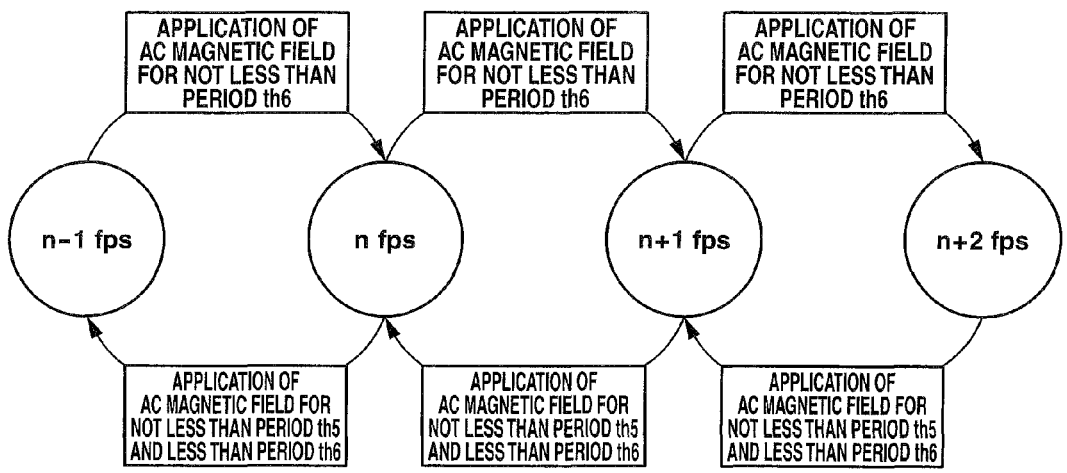
FIG. 11 is a operation state transition diagram in the third embodiment.

FIG. 9A to FIG. 11 relate to a third embodiment of the living-body observation system of the present invention, in which FIGS. 9A to 9D are waveform diagrams to show the operation waveforms of respective principal parts in a case in which the frame rate of the image pickup section 5 is increased during operation, FIGS. 10A to 10D are waveform diagrams to show the operation waveforms of respective principal parts in a case in which the frame rate of the image pickup section 5 is decreased during operation, and FIG. 11 shows an operational state transition diagram in the third embodiment, respectively.

The living-body observation system 1 of the third embodiment is configured in substantially the same manner with the first embodiment. Moreover, in the present embodiment, the control section 16 can change the frame rate of the image pickup section 5 for the capsule endoscope 2 in operation.

Either when the capsule endoscope 2 in operation is present outside the body before being swallowed by an examinee, or when the capsule endoscope 2 is swallowed and present inside a body cavity of the examinee, the case of changing the frame rate of the capsule endoscope 2 that is operating at a predetermined frame rate will be described by using FIGS. 9A to 11.

First, the case of increasing the frame rate of the image pickup section 5 will be described in FIGS. 9A to 9D.

It is noted that FIG. 9A shows an AC magnetic field generation state from the magnetic field generating section 3, FIG. 9B shows an input signal (N1) of the control section 16, FIG. 9C shows an output signal (N3) of the control section 16 to be inputted to the in-vivo information acquiring section, and FIG. 9D shows the image pickup timing of the capsule endoscope, respectively.

The control section 16 generates pulses at a rate of once per second and outputs them to the image pickups section 5 as shown in the output signal (node N3) of the control section 16 of FIG. 9C so that the capsule endoscope 2 is operating at 1 fps (see FIG. 9D).

If the magnetic field generating section 3 is driven during a period th51 from time t81 to time t82 for the capsule endoscope 2 which is operating at 1 fps, an AC magnetic field is generated from the magnetic field generating section 3 and is applied to the capsule endoscope 2 (see FIG. 9A).

When the AC magnetic field is applied to the capsule endoscope 2, the output of the magnetic field detection section 8 provided in the capsule endoscope 2 becomes a "High" level, that is, the input signal (node N1) of the control section 16 becomes a "High" level as well.

When the input signal (node N1) from the magnetic field detection section 8 becomes a "High" level, the control section 16 monitors the period of this "High" level.

It is noted that the period th51 in which an AC magnetic field is generated from the magnetic field generating section 3 will become longer than a predetermined period th6. Moreover, the period th6 is a period in which the application time of the AC magnetic field applied to the capsule endoscope 2 is measured and the frame rate is controlled. When the control of the third embodiment is used in combination with the control of the second embodiment, the period th6 is set to be longer than the period th5 in the second embodiment.

In this case, the control section 16 provided in the capsule endoscope 2 judges that the number of images taken by in one second is to be increased, that is, the frame rate of the image pickup section 5 is to be increased, since the application period in which an AC magnetic field is applied to the capsule endoscope 2 is not less than the period th6.

Therefore, the control section 16 generates two pulses in one second at and after time t83 so that the number of images to be taken in one second is increased by one step to be set at 2 fps.

Thus, by applying an AC magnetic field to the capsule endoscope 2 in operation for a period longer than the period ph6 which is a predetermined period, it is made possible to increase the frame rate to more than the frame rate of the image pickup section 5 which is currently operating.

Next, the case of decreasing the frame rate of the image pickup section 5 will be described in FIGS. 10A to 10D.

It is noted that FIG. 10A shows an AC magnetic field generation state from the magnetic field generating section 3, FIG. 10B shows an input signal (N1) of the control section 16, FIG. 10C shows an output signal (N3) of the control section 16 to be inputted to the in-vivo information acquiring section, and FIG. 10D shows the image pickup timing of the capsule endoscope, respectively.

The control section 16 generates pulses at a rate of twice per second and outputs them to the image pickups section 5 as shown in the output signal (node N3) of the control section 16 of FIG. 10C so that the capsule endoscope 2 is operating at 2 fps (see FIG. 10D).

If the magnetic field generating section 3 is driven during a period th61 from time t91 to time t92 for the capsule endoscope 2 which is operating at 2 fps, an AC magnetic field is generated from the magnetic field generating section 3 to be applied to the capsule endoscope 2 (see FIG. 10A).

When the AC magnetic field is applied to the capsule endoscope 2, the output of the magnetic field detection section 8 provided in the capsule endoscope 2 becomes a "High" level, that is, the input signal (node N1) of the control section 16 becomes a "High" level as well.

When the input signal (node N1) from the magnetic field detection section 8 becomes a "High" level, the control section 16 monitors the period of this "High" level.

In the case of FIGS. 10A to 10D, the period th61, in which an AC magnetic field is generated from the magnetic field generating section 3, is longer than the period th5 and is shorter than the period th6.

In this case, the control section 16 provided in the capsule endoscope 2 judges that the number of images taken in one second is to be decreased, that is, the frame rate of the image pickup section 5 is to be decreased, since the application period in which an AC magnetic field is applied to the capsule endoscope 2 is less than the period th6.

Therefore, the control section 16 generates one pulse in one second at and after time t93 so that the number of images to be taken in one second is decreased by one step to be set at 1 fps.

Thus, by applying an AC magnetic field to the capsule endoscope 2 in operation for a period longer than the period th5 which is a predetermined period and shorter than the period th6, it is made possible to decrease the frame rate to less than the frame rate of the image pickup section 5 which is currently operating.

FIG. 11 shows a transition diagram of the operation state of increasing/decreasing the frame rate relating the above described third embodiment.

As shown in FIG. 11, the application of an AC magnetic field to the capsule endoscope 2, which is operating at a predetermined frame rate (n is an integer), for a period not less than the period th6 will increase the frame rate by one, and on the contrary, the application of an AC magnetic field for a period longer than the period th5 and less than the period th6 will decrease the frame rate by one.

Thus, the control section 16 of the third embodiment can increase/decrease the frame rate in accordance with the period in which an AC magnetic field is applied to the capsule endoscope 2 in operation.

It is noted that although the increase/decrease of the frame rate is performed by unit of one frame in FIG. 11, the increase/decrease range is not necessarily by unit of one frame, and any increase/decrease range may be set as desired, for example, the frame rate may be changed by unit of 2 frames.

Moreover, although in the third embodiment, it is configured such that when the period in which an AC magnetic field is applied is longer than a prescribed and predetermined period, the frame rate is increased, and when shorter than the prescribed and predetermined period, the frame rate is decreased, such setting is not necessarily required, and the configuration may be such that when the period in which an AC magnetic field is applied is longer than a prescribed and predetermined period, the frame rate is decreased, and when shorter than the prescribed and predetermined period, the frame rate is increased.

In this way, since the living-body observation system 1 of the third embodiment can increase/decrease the frame rate even while in operation, by applying an AC magnetic field to the capsule endoscope 2, it is possible to increase/decrease the frame rate at any time in accordance with the observation result even after the capsule endoscope 2 is swallowed.

Further, although the living-body observation system 1 of the third embodiment has been described in a case in which the frame rate is increased/decreased in accordance with the period in which an AC magnetic field is applied to the capsule endoscope 2 in operation, the frame rate of the capsule endoscope 2 in operation can also be increased/decreased in accordance with the number of times an AC magnetic field is applied within a predetermined period as with the first embodiment Therefore, according to the third embodiment, it becomes possible to control the frame rate in accordance with the period in which an AC magnetic field is applied to the capsule endoscope 2 in operation, or the number of times an AC magnetic field is applied within a predetermined period, thereby allowing the frame rate to be controlled in accordance with the situation of the site to be observed even after an examinee has swallowed the capsule endoscope 2. Other advantages are similar to those of the first and second embodiments.

It is noted that although in the above described embodiments, a capsule endoscope 2 that includes only one illumination section 4 and one image pickup section 5 has been described as the capsule endoscope 2; for example, the present invention can be applied to a twin-lens capsule endoscope 2 that includes a plurality of illumination sections 4 and image pickup sections.

Further, the magnetic field detection section 8 to be installed in the in-vivo observation apparatus does not need to have the above described circuit configuration, and it is obvious that other circuit configurations can be applied provided that similar operation can be achieved.

Moreover, the pattern of AC magnetic field is not necessarily the pattern of AC magnetic field as in the invention described above, other patterns can be applied if the pattern of AC magnetic field to be applied and the frame rate are specified in advance in the magnetic field generating section 3 and the capsule endoscope 2

Furthermore, although in the above described embodiments, the configuration in which a capsule endoscope 2 is used as the living-body observation system has been described, the present invention can be applied to other in-vivo observation systems, for example, a pH observation system, etc., and for example, the present invention is applicable to a case in which the timing of measurement is changed.

The present invention will not be limited to the above described embodiments, and may be implemented with various modifications within the range not departing from the essence of the invention.

What is claimed is:

1. A living-body observation system, comprising:
    an in-vivo observation apparatus including:
        an in-vivo information acquiring section that includes an image pickup section and acquires information in a living body;
        a power source section that supplies driving power of the in-vivo information acquiring section;
        a magnetic field detection section that detects a magnetic field from outside and outputs a detected result as an electric signal; and
        a power supply control section that controls a supply state of driving power supplied from the power source section to the in-vivo information acquiring section, and an operation of the in-vivo information acquiring section, based on the electric signal; and
    a magnetic field generating section that is disposed outside the in-vivo observation apparatus and generates the magnetic field; wherein
    the power supply control section includes a control section that sets a frame rate of the image pickup section based on a count value of a number of a plurality of applications of the magnetic field detected by the magnetic field detection section during a predetermined period of time.

2. The living-body observation system according to claim 1, wherein the in-vivo observation apparatus is a capsule endoscope.

3. A driving method for driving a living-body observation system, wherein the living-body observation system comprises:
    an in-vivo observation apparatus including:
        an in-vivo information acquiring section that includes an image pickup section and acquires information in a living body;
        a power source section that supplies driving power of the in-vivo information acquiring section;
        a magnetic field detection section that detects a magnetic field from outside and outputs a detected result as an electric signal; and
        a power supply control section that controls a supply state of driving power supplied from the power source section to the in-vivo information acquiring section, and an operation of the in-vivo information acquiring section, based on the electric signal; and
    a magnetic field generating section that is disposed outside the in-vivo observation apparatus and generates the magnetic field;
    wherein the method comprises setting a frame rate of the image pickup section based on a count value of a number of a plurality of applications of the magnetic field detected by the magnetic field detection section during a predetermined period of time.

4. The driving method according to claim 3, wherein the in-vivo observation apparatus is a capsule endoscope.

5. A living-body observation system, comprising:
    an in-vivo observation apparatus including:
        an in-vivo information acquiring section that includes an image pickup section and acquires information in a living body;
        a power source section that supplies driving power of the in-vivo information acquiring section;
        a magnetic field detection section that detects a magnetic field from outside and outputs a detected result as an electric signal; and
        a power supply control section that controls a supply state of driving power supplied from the power source section to the in-vivo information acquiring section, and an operation of the in-vivo information acquiring section, based on the electric signal; and
    a magnetic field generating section that is disposed outside the in-vivo observation apparatus and generates the magnetic field; wherein
    the power supply control section includes a control section that sets a frame rate of the image pickup section based on a comparison between: (a) a length of an application period of time of the magnetic field detected by the magnetic field detection section; and (b) a length of a predetermined period of time which has been set in the living-body observation system at a time before the comparison.

6. The living-body observation system according to claim 5, wherein the control section sets a frame rate of the image pickup section based on a comparison between: (a) the length of the application period of time of the magnetic field detected by the magnetic field detection section; and (b) the length of the predetermined period of time which has been set in the living-body observation system at a time before the comparison, wherein the length of the predetermined period of time is used for the comparison as a length of a period of a time after a starting time of the application period of time of the magnetic field detected by the magnetic field detection section.

7. The living-body observation system according to claim 5, wherein the predetermined period of time includes a first predetermined period of time and a second predetermined period of time.

8. The living-body observation system according to claim 7, wherein the control section sets a frame rate of the image pickup section based on a comparison between: (a) the length of the application period of time of the magnetic field detected by the magnetic field detection section; and (b) each of the first predetermined period of time and the second predetermined period of time.

9. The living-body observation system according to claim 5, wherein the in-vivo observation apparatus is a capsule endoscope.

10. The living-body observation system according to claim 5, wherein the control section sets a frame rate of the image pickup section based on a comparison between: (a) the length of the application period of time of the magnetic field detected by the magnetic field detection section; and (b) the length of the predetermined period of time which has been set in the in-vivo observation apparatus at a time before the comparison.

11. A driving method for driving a living-body observation system, wherein the living-body observation system comprises:
   an in-vivo observation apparatus including:
      an in-vivo information acquiring section that includes an image pickup section and acquires information in a living body;
      a power source section that supplies driving power of the in-vivo information acquiring section;
      a magnetic field detection section that detects a magnetic field from outside and outputs a detected result as an electric signal; and
      a power supply control section that controls a supply state of driving power supplied from the power source section to the in-vivo information acquiring section, and an operation of the in-vivo information acquiring section, based on the electric signal; and
   a magnetic field generating section that is disposed outside the in-vivo observation apparatus and generates the magnetic field;
   wherein the method comprises setting a frame rate of the image pickup section based on a comparison between: (a) a length of an application period of time of the magnetic field detected by the magnetic field detection section and; (b) a length of a predetermined period of time which has been set in the living-body observation system at a time before the comparison.

12. The driving method according to claim 11, wherein the frame rate is set based on a comparison between: (a) the length of the application period of time of the magnetic field detected by the magnetic field detection section; and (b) the length of the predetermined period of time which has been set in the living-body observation system at a time before the comparison, wherein the length of the predetermined period of time is used for the comparison as a length of a period of a time after a starting time of the application period of time of the magnetic field detected by the magnetic field detection section.

13. The driving method according to claim 12, wherein the predetermined period of time includes a first predetermined period of time and a second predetermined period of time.

14. The driving method according to claim 13, wherein the frame rate is set based on a comparison between: (a) the length of the application period of time of the magnetic field detected by the magnetic field detection section; and (b) each of the first predetermined period of time and the second predetermined period of time.

15. The driving method according to claim 11, wherein the in-vivo observation apparatus is a capsule endoscope.

16. The driving method according to claim 11, wherein the frame rate is set based on a comparison between: (a) the length of the application period of time of the magnetic field detected by the magnetic field detection section; and (b) the length of the predetermined period of time which has been set in the in-vivo observation apparatus at a time before the comparison.

* * * * *